United States Patent
Min et al.

(10) Patent No.: US 6,975,903 B1
(45) Date of Patent: Dec. 13, 2005

(54) RATE ADAPTIVE PACEMAKER USING IMPEDANCE MEASUREMENTS AND STROKE VOLUME CALCULATIONS

(75) Inventors: Mart Min, Tallinn (EE); Andres Kink, Harjumma (EE); Toomas Parve, Tallinn (EE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 09/937,875

(22) PCT Filed: Mar. 23, 2000

(86) PCT No.: PCT/SE00/00572

§ 371 (c)(1),
(2), (4) Date: Oct. 1, 2002

(87) PCT Pub. No.: WO00/57953

PCT Pub. Date: Oct. 5, 2000

(30) Foreign Application Priority Data

Mar. 31, 1999 (SE) .................................. 9901194

(51) Int. Cl.$^7$ ............................................. A61N 1/365
(52) U.S. Cl. ............................. 607/24; 607/28; 607/17
(58) Field of Search ................................ 607/9, 17–18, 607/24, 28

(56) References Cited

U.S. PATENT DOCUMENTS

| | | | |
|---|---|---|---|
| 4,535,774 A | 8/1985 | Olson | 607/24 |
| 5,154,171 A | 10/1992 | Chirife | 607/24 |
| 5,183,040 A | 2/1993 | Nappholz et al. | 607/4 |
| 5,280,429 A | 1/1994 | Withers | 378/70 |
| 5,282,840 A | 2/1994 | Hudrlik | 607/28 |
| 5,413,592 A * | 5/1995 | Schroeppel | 607/18 |
| 5,807,272 A | 9/1998 | Kun et al. | 600/547 |
| 5,861,011 A | 1/1999 | Stoop | 607/25 |

FOREIGN PATENT DOCUMENTS

| | | | |
|---|---|---|---|
| EP | 0 140 472 | 5/1985 | A61N 1/36 |
| EP | 0 576 114 | 12/1993 | A61N 1/365 |

OTHER PUBLICATIONS

"Design of Cardiac Pacemakers," Webster, Ed., IEEE Press (1995), pp. 380-386.

* cited by examiner

*Primary Examiner*—Carl Layno
(74) *Attorney, Agent, or Firm*—Schiff Hardin LLP

(57) ABSTRACT

A rate adaptive pacemaker comprises a means (2) for determining the demand of the patient's organism, a pacing rate controlling means (16) for controlling the pacing rate in response to the patient's demand, and a pacing rate limiting means (20) for preventing the pacing rate from becoming too low. The pacing rate limiting means is adapted to limit the pacing rate downwards such that a first predetermined relation is satisfied between actual cardiac output (CO) and cardiac output ($CO_{rest}$) for the patient in rest conditions and a second predetermined relation is satisfied between actual stroke volume (SV) and rest stroke volume ($SV_{rest}$).

6 Claims, 1 Drawing Sheet

RATE ADAPTIVE PACEMAKER USING IMPEDANCE MEASUREMENTS AND STROKE VOLUME CALCULATIONS

BACKGROUND OF THE INVENTION

1. Field of the Invention

The present invention relates to a rate adaptive pacemaker of the type having an arrangement for determining the demand of the patient's organism, a pacing rate control for controlling the pacing rate in response to the patient's demand, and a pacing rate limiter for preventing the pacing rate from becoming too low.

2. Description of the Prior Art

The pacing rate of a rate adaptive pacemaker may become too low due to the physical demand of the patient's organism and heart. This may result in lack of oxygen supply to the myocardium. Under certain conditions the heart may not be able to fulfil the physiological needs of the patient's organism and heart if the pacing rate is not limited.

It is known to set a lower limit for the pacing rate. This limit value is normally determined from the patient's diagnosis and a constant or externally programmable limit can be set. Thus U.S. Pat. No. 4,535,774 describes a stroke volume controlled pacemaker, in which the heart rate is permitted to range between prescribed minimum and maximum heart rate values. Further, in U.S. Pat. No. 5,861,011 a pacemaker is disclosed having a system for determining the circadian rhythm by examining variations in the QT interval and adjusting the pacemaker night time setting of a lower rate limit to the lower value than the pacemaker daytime setting of the lower rate limit. In U.S. Pat. No. 5,183,040, an antitachycardia pacer is disclosed which analyzes cardiac output information for assessing hemodynamic status and determining adequate blood supply.

Thus, a pacing rate that is too low may cause an influx of blood enriched with oxygen that also is too low. A prescribed suitable lower pacing rate limit avoids the slow influx of the fresh blood. At the same time this lower limit value should be low enough so as to not to disturb a peaceful sleep. In that case the patient can feel more healthy in various everyday life conditions including peaceful sleeping.

SUMMARY OF THE INVENTION

An object of the present invention is to provide a rate adaptive pacemaker in which the pacing rate is prevented from becoming too low, such that the above discussed inconveniences for the patient are avoided.

The above object is achieved in accordance with the principles of the present invention in a rate adaptive pacemaker having an arrangement adapted for interaction with a subject for obtaining an electrical signal representing cardiac demand of the subject, a computing unit supplied with the signal for calculating an actual cardiac output CO and a cardiac output $CO_{rest}$ for the subject at rest, a pacing rate controller also supplied with the signal for generating, as an output, a pacing rate dependent on the cardiac demand, and a pacing rate limiter connected to the computing unit and to the pacing rate controller for downwardly limiting the pacing rate, wherein the pacing rate limiter calculates a stroke volume SV and a stroke volume $SV_{rest}$ for the subject at rest, and downwardly limits the pacing rate so that a first predetermined relation $CO > CO_{rest}$ and a second predetermined relation $SV/SV_{rest} < L$ are satisfied, wherein L is a predetermined constant in a range between 1.2 and 1.5.

Thus, by satisfying two predetermined relations the pacemaker according to the invention ensures a sufficient minimum energy supply to the patient's organism or body and at the same time the maximum value of the stroke volume is limited and these conditions are continuously automatically checked.

In one embodiment of the pacemaker 20 according to the invention the first predetermined relation is $$CO > CO_{rest} \quad (1)$$

and the second predetermined relation is $$(SV)/(SV_{rest}) < L \quad (2)$$

where L denotes a predetermined constant >1, preferably equal to a value between 1.2 and 1.5. In this way it is ensured that the actual cardiac output will not become lower than the rest state cardiac output $CO_{rest}$ as well as ensuring that the actual stroke volume will be less than a maximum allowed value equal to $L \times SV_{rest}$, where L typically has a value between 1.2 and 1.5, depending on the health of the patient's myocardium. By satisfying both these conditions simultaneously a physiologically well founded heart work management at low work loads is ensured.

In another embodiment of the pacemaker according to the invention the pacing rate limiter includes a lower limit setting unit for setting a lower limit value for the pacing rate, and a lower limit determining unit for determining the relation between actual cardiac output (CO) and cardiac output ($CO_{rest}$) for the patent in rest conditions, and the relation between actual stroke volume (SV) and a rest stroke volume ($SV_{rent}$) and for calculating a lower pacing rate limit value from the relations for supply to said limit setting unit. The lower limit determining unit includes a stroke volume measuring unit for measuring actual stroke volume SV and a comparator for comparing measured actual stroke volume SV with stroke volume $SV_{rest}$ for the patient in rest conditions to ensure that the inequality $$SV/SV_{rest} < L \quad (3)$$

is satisfied. The lower limit determining unit is adapted to calculate a lower pacing rate limit value from the equation $$\text{lower pacing rate limit} = HR_{rest}(S_{Vrest}/SV) \quad (4)$$

where $HR_{rest}$ denotes the heart rate for the patient in rest conditions, provided that said inequality is satisfied. In this way the lower pacing rate limit is continuously automatically calculated and it may also happen that the lower pacing rate limit becomes lower than the typical heart rate $HR_{rest}$ for rest conditions of the patient.

In another embodiment of the pacemaker according to the invention a bioimpedance measurement unit is provided to measure the cardiac bioimpedance as a function of time for determining therefrom actual cardiac output CO and actual stroke volume SV from the measured cardiac bioimpedance. These parameters thus are obtained in an easy and reliable way from the time variation of the bioimpedance measured between a standard intracardiac electrode and the housing of the pacemaker, when an excitation current proceeds from the electrode tip.

DESCRIPTION OF THE PREFERRED EMBODIMENTS

Figure 1:
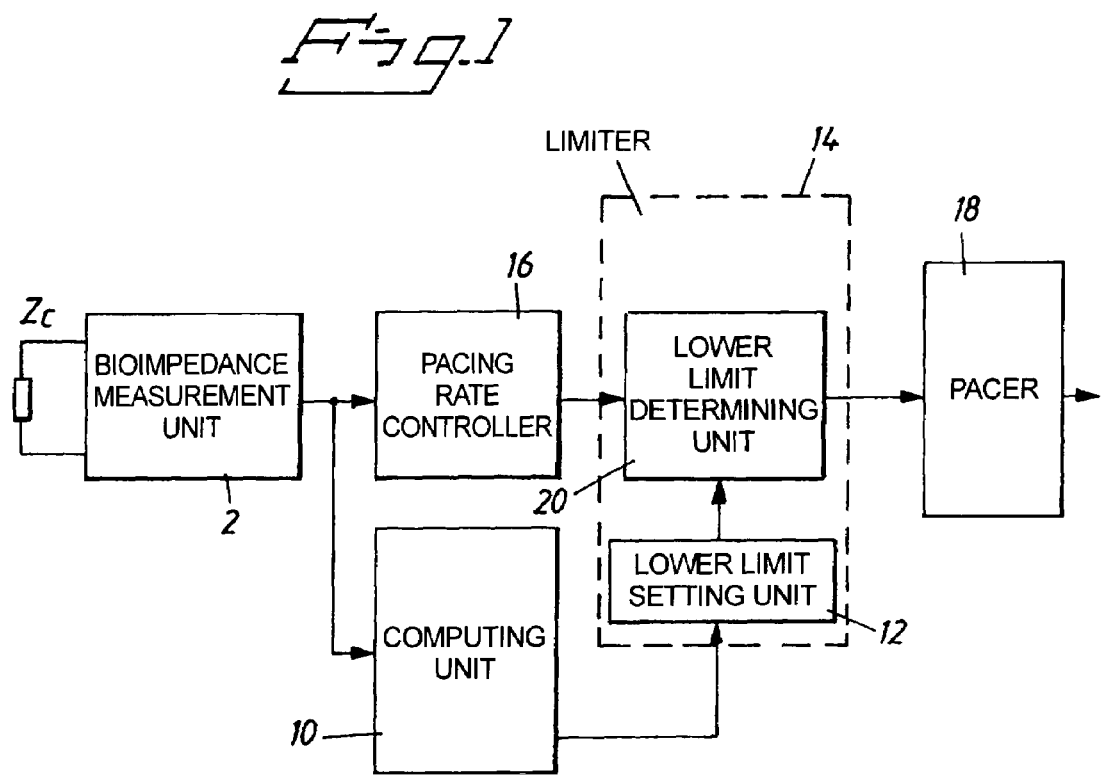
FIG. 1 is a schematic block diagram of a rate adaptive pacemaker constructed and operating in accordance with the principles of the present invention.

To avoid the current cardiac output CO $$CO=SV \times HR \qquad (5)$$

becomes lower than the rest state cardiac output $CO_{rest}$ the pacing rate must be above a lower pacing rate limit given by $$\text{lower pacing rate limit} = (C_{Orest})/(SV) \qquad (6)$$

and since $$CO_{rest} = HR_{rest} \times S_{Vrest} \qquad (7)$$

$$\text{lower pacing rate limit} = (HR_{rest}) \times (S_{Vrest}/SV) \qquad (8)$$

In addition the maximum value of the stroke volume must be limited, i.e.

$$SV < L \times S_{Vrest} \qquad (9)$$

Thus, the following two conditions must be fulfilled simultaneously for insuring a physiologically well founded heart work management at low work loads.

$$\text{Pacing rate limit} > (HR_{rest}) \times (S_{Vrest}/SV) \qquad (10)$$

$$SV/SV_{rest} < L \qquad (11)$$

where L is a constant typically equal to a value of 1.2 to 1.5, depending on the health of the patient's myocardium.

Thus the lower pacing rate limit is continuously automatically calculated from the measured actual stroke volume SV and known values of $SV_{rest}$, $HR_{rest}$ and the constant L. The actual stroke volume can be determined from e.g. bioimpedance measurements as will be described below.

Figure 2:
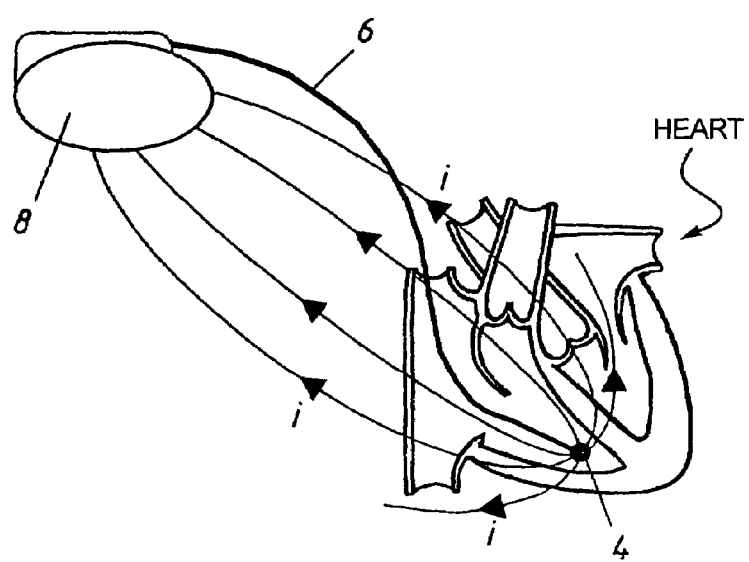
FIG. 2 illustrates the principle of bioimpedance measurements between the tip of an intracardial electrode and the metallic housing of the pacemaker, these measurements being used in the rate adaptive pacemaker of FIG. 1.

FIG. 1 is a block diagram of an embodiment of the pacemaker according to the invention having a bioimpedance measurement unit 2 for measuring the time variation of the electric intracardiac bioimpedance $Z_e(t)$. This type of measurement is well-known, see e.g. "Design of Cardiac Pacemakers", edited by John G. Webster, IEEE Press, 1995, pp. 380–386 and U.S. Pat. Nos. 5,154,171, 5,280,429, 5,282,840 and 5,807,272. Thus the time variation of the intracardiac bioimpedance can be measured between the tip 4 of the intracardial electrode 6 and the housing 8 of the pacemaker, when an excitation current is fed from the electrode tip 4, as schematically illustrated in FIG. 2. Thus a standard pacing lead can be used for this measurement.

From the measured time variations AZc(t) the stroke volume SV needed for calculating the lower pacing rate limit according to equation (8) above, or for checking the inequalities (10) or (11), are determined in a computing unit 10, see FIG. 1.

The calculated lower limit value is supplied to a lower limit 30 setting unit 12 of a pacing rate limiter 14.

A pacing rate controller 16 is also provided for controlling the pacing rate of the pacer or pulse generator 18 in response to the patient's demands. In a limiting unit 20 of the limiter 14 the demanded pacing rate is compared to the set lower limit pacing rate and the actual pacing rate is limited to the set lower limit value if the demanded pacing rate reaches this limit value. Thus in the pacemaker according to the invention a lower limit value for the pacing rate is continuously automatically determined and it is continuously automatically verified that the actual pacing rate does not exceed the present lower limit value.

Alternatively, the pacemaker can be modified to continuously monitor that the inequalities (10) or (11) above are satisfied.

Above bioimpedance measurements are described for determining the stroke volume SV. This parameter can, however, also be determined by other techniques, like by ECG measurements, by ultrasound technique, by radiometric and optical techniques etc. Generally all dynamic distance and/or capacity measuring methods are applicable.

Although modifications and changes may be suggested by those skilled in the art, it is the intention of the inventors to embody within the patent warranted hereon all changes and modifications as reasonably and properly come within the scope of their contribution to the art.

We claim:

1. A rate adaptive pacemaker comprising:
   an arrangement adapted for interaction with a subject for obtaining an electrical signal representing cardiac demand of said subject;
   a computing unit supplied with said signal for calculating an actual cardiac output CO, and a cardiac output $CO_{rest}$ for said subject at rest;
   a pacing rate controller also supplied with said signal for generating, as an output, a pacing rate dependent on said cardiac demand; and
   a pacing rate limiter connected to said computing unit and to said pacing rate controller for downwardly limiting said pacing rate, said pacing rate limiter calculating a stroke volume SV and a stroke volume $SV_{rest}$ for said subject at rest, and downwardly limiting said pacing rate so that a first predetermined relation $CO > CO_{rest}$ and a second predetermined relation $SV/SV_{rest} < L$ are satisfied, wherein L is a predetermined constant in a range between 1.2 and 1.5.

2. A rate adaptive pacemaker as claimed in claim 1 wherein said pacing rate limiter comprises a lower limit setting unit for setting a lower limit value for said pacing rate and a lower limit determining unit wherein SV and $SV_{rest}$ are determined, and wherein a relation between CO and $CO_{rest}$ and a relation between SV and $SV_{rest}$ are determined, and for calculating a lower pacing rate limit value from said relations for supply to said limit setting unit.

3. A rate adaptive pacemaker as claimed in claim 2 wherein said lower limit determining unit includes a comparator for comparing $SV/SV_{rest}$ to L to ensure that (SV/$SV_{rest}$) < is satisfied, and for calculating said lower pacing rate limit value as a product of $HR_{rest}$ and $Sv_{rest}/SV$), wherein $HR_{rest}$ is a heart rate for said subject at rest, provided $(SV/SV_{rest}) < L$ is satisfied.

4. A rate adaptive pacemaker as claimed in claim 1 wherein said arrangement for determining cardiac demand comprises a bioimpedance measuring unit adapted to measure a cardiac bioimpedance as a function of time as said signal representing cardiac demand.

5. A rate adaptive pacemaker as claimed in claim 1 wherein said arrangement for determining cardiac demand comprises an ECG measuring unit for generating an ECG signal as said signal representing cardiac demand.

6. A rate adaptive pacemaker as claimed in claim 1 wherein said arrangement for determining cardiac demand is a dynamic distance measuring unit which generates a distance signal as said signal representing cardiac demand.

* * * * *